United States Patent
Brown

(10) Patent No.: US 9,881,778 B2
(45) Date of Patent: Jan. 30, 2018

(54) HYBRID ACQUISITION METHOD INCORPORATING MULTIPLE DISSOCIATION TECHNIQUES

(71) Applicant: MICROMASS UK LIMITED, Wilmslow (GB)

(72) Inventor: Jeffery Mark Brown, Hyde (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/304,668

(22) PCT Filed: Apr. 17, 2015

(86) PCT No.: PCT/GB2015/051162
§ 371 (c)(1),
(2) Date: Oct. 17, 2016

(87) PCT Pub. No.: WO2015/159096
PCT Pub. Date: Oct. 22, 2015

(65) Prior Publication Data
US 2017/0069475 A1    Mar. 9, 2017

(30) Foreign Application Priority Data

Apr. 17, 2014  (EP) .................................... 14165253
Apr. 17, 2014  (GB) .................................. 1406981.9

(51) Int. Cl.
H01J 49/00       (2006.01)
G01N 27/62       (2006.01)
H01J 49/42       (2006.01)

(52) U.S. Cl.
CPC ........ H01J 49/0031 (2013.01); G01N 27/622 (2013.01); H01J 49/004 (2013.01); H01J 49/005 (2013.01); H01J 49/0072 (2013.01); H01J 49/421 (2013.01)

(58) Field of Classification Search
CPC ............... H01J 49/0027; H01J 49/0031; H01J 49/0072; H01J 49/26; H01J 49/421; H01J 49/4215; H01J 49/4225; G01N 27/622
See application file for complete search history.

(56) References Cited

U.S. PATENT DOCUMENTS

| | | | |
|---|---|---|---|
| 6,107,623 A | 8/2000 | Bateman et al. | |
| 6,717,130 B2 | 4/2004 | Bateman et al. | |
| 7,309,860 B2 | 12/2007 | Baba et al. | |
| 7,586,089 B2 | 9/2009 | Hartmer | |
| 7,829,845 B2 | 11/2010 | Deguchi et al. | |
| 7,906,759 B2 * | 3/2011 | Manri ................. | H01J 49/0045 250/281 |

(Continued)

FOREIGN PATENT DOCUMENTS

| | | |
|---|---|---|
| GB | 2523222 | 8/2015 |
| WO | 2011/058381 | 3/2011 |

*Primary Examiner* — David E Smith

(57) ABSTRACT

A method is disclosed wherein parent or precursor ions are fragmented or reacted according to a first fragmentation or reaction mode, and when an ion of interest is detected the method then temporarily switches to a second mode of fragmentation or reaction. This enables a full un-biased MS/MS data set to be provided over a wide mass to charge ratio range with high-duty cycle, together with complementary detailed fragment data of interest, in a single experimental run or acquisition.

20 Claims, 3 Drawing Sheets

(56) References Cited

U.S. PATENT DOCUMENTS

| | | |
|---|---|---|
| 8,153,961 B2 | 4/2012 | Zabrouskov |
| 8,168,943 B2 | 5/2012 | Schwartz et al. |
| 9,190,251 B2 | 11/2015 | Green et al. |
| 9,255,906 B2 | 2/2016 | Williams et al. |
| 9,347,917 B2 | 3/2016 | Campbell et al. |
| 9,460,902 B2 | 10/2016 | Wildgoose |
| 9,508,537 B2 | 11/2016 | Brown et al. |
| 2008/0048109 A1* | 2/2008 | Schwartz ............ H01J 49/0031 250/282 |
| 2011/0049351 A1* | 3/2011 | Zabrouskov ....... G01N 33/6848 250/282 |

* cited by examiner

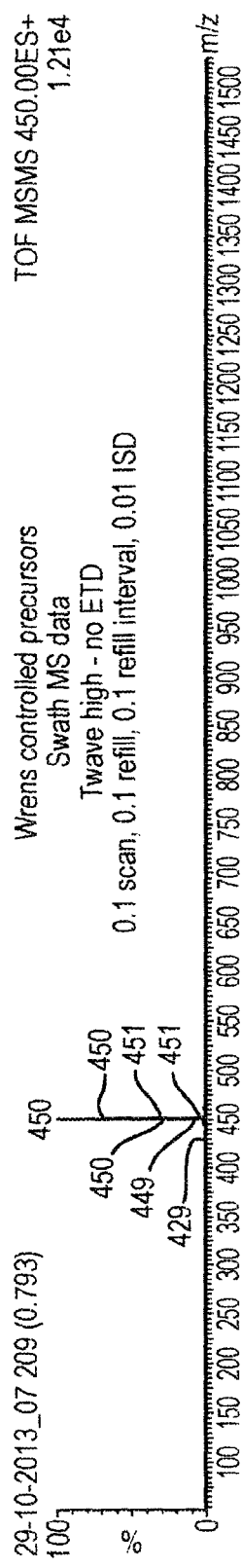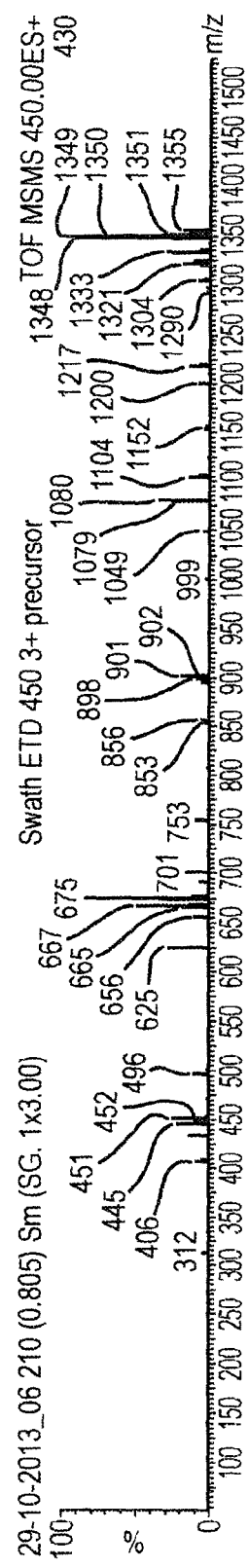

HYBRID ACQUISITION METHOD INCORPORATING MULTIPLE DISSOCIATION TECHNIQUES

CROSS-REFERENCE TO RELATED APPLICATIONS

This application represents a National Stage of International Application No. PCT/GB2015/051162 entitled "Hybrid Acquisition Method Incorporating Multiple Dissociation Techniques" filed 17 Apr. 2015 which claims priority from and the benefit of United Kingdom patent application No. 1406981.9 filed on 17 Apr. 2014 and European patent application No. 14165253.7 filed on 17 Apr. 2014. The entire contents of these applications are incorporated herein by reference.

BACKGROUND TO THE PRESENT INVENTION

The present invention relates to a method of mass spectrometry and a mass spectrometer.

It is known to employ Data Dependant Acquisitions ("DDA") on a tandem mass spectrometer such as a quadrupole-Time of Flight mass spectrometer ("Q-ToF"). According to such known techniques the mass to charge ratios of parent or precursor ions are determined in an initial survey scan. A quadrupole mass filter is then arranged to sequentially isolate each individual parent or precursor ion in turn according to its mass to charge ratio and then to accelerate the selected parent or precursor ions into a collision cell in order to fragment the parent or precursor ions so as to produce product or fragment ions by Collision Induced Dissociation ("CID").

The product or fragment ions are then mass analysed using a Time of Flight mass analyser. However, when parent or precursor ions are isolated by the mass filter then other parent or precursor ions will be discarded. As a result, the known mass spectrometer and method of operation suffers from a relatively low duty cycle.

The known method of selecting parent or precursor ions also suffers from the problem that it will result in some bias. For example, if the 20 most intense parent or precursor ions are selected then this will bias the data towards the most abundant species.

An improvement on the above described known approach is disclosed in U.S. Pat. No. 6,717,130 (Micromass) which discloses an approach wherein parent or precursor ions are not isolated and selected but rather fragment ions are assigned to parent ions by correlating their detection times to the times at which corresponding parent species elute from a chromatography column. This technique results in an improved duty cycle and minimises any bias in the acquisitions.

It is also known to operate a quadrupole-Time of Flight mass spectrometer by operating the quadrupole mass filter in a low-resolution mode with a transmission window of, for example, 25 Da. The mass to charge ratio range of the ions transmitted by the quadrupole mass filter is then sequentially incremented in steps of approximately 25 Da and in a manner that is not data dependant.

Ions exiting the quadrupole mass filter are accelerated into a gas cell so as to fragment by Collision Induced Dissociation and the resulting fragment ions are mass analysed by the Time of Flight mass analyser. The data from each 25 Da window is kept separate for processing. This technique is unbiased in the nature of the acquisition and has an improved duty cycle compared with other arrangements operating with narrower mass to charge ratio isolation windows.

The two Data Independent Acquisition ("DIA") methods discussed above typically fragment parent or precursor ions using fragmentation methods that are particularly suited for fragmenting parent or precursor ions over a wide mass to charge ratio range. In particular, a Collision Induced Dissociation ("CID") fragmentation cell is commonly used to fragment ions since Collision Induced Dissociation fragmentation is suitable for fragmenting ions having a wide range of mass to charge ratios.

However, fragmentation methods such as Collision Induced Dissociation tend to be limited in the types of fragmentation that they can induce and therefore in the fragment ion spectra that they can produce. As a result, this limits the information that can be obtained. For example, in the analysis of post translationally modified ("PTM") peptides Collision Induced Dissociation methods give little information other than the loss of the side chain.

It is known that other types of fragmentation can advantageously induce different types of fragmentation in parent or precursor ions and can therefore produce different fragment ions from the same parent or precursor ion. These fragment ions can be useful in a number of applications. In particular, Electron Transfer Dissociation ("ETD") is known to be particularly useful in the analysis of post translationally modified peptides.

However, seeking to fragment parent or precursor ions having potentially a wide mass to charge ratio range using an Electron Transfer Dissociation fragmentation device is problematic and fragmentation can be curtailed entirely due to an excessive amount of charge flowing through the Electron Transfer Dissociation reaction cell. This arises due to the necessity for there to be a surplus of reagent anions available to react with analyte cation charges or else the analyte cation charges tend to neutralise the reagent anions thereby rendering the Electron Transfer Dissociation reaction unviable.

It is therefore desired to provide and improved method of mass spectrometry and an improved mass spectrometer.

SUMMARY OF THE PRESENT INVENTION

From a first aspect the present invention provides a method of mass spectrometry comprising:

mass filtering parent or precursor ions with a mass filter;

transmitting the mass filtered parent or precursor ions into a fragmentation or reaction device operating in a first fragmentation or reaction mode;

fragmenting or reacting the parent or precursor ions in the fragmentation or reaction device operating in the first fragmentation or reaction mode so as to produce first fragment or product ions;

wherein the mass to charge ratio, or range of mass to charge ratios, of the parent or precursor ions transmitted by the mass filter is varied with time such that parent or precursor ions of different mass to charge ratios are fragmented or reacted by the first fragmentation or reaction mode at different times;

monitoring for the detection of parent or precursor ions of interest and/or first fragment or product ions of interest, and wherein if parent or precursor ions of interest and/or first fragment or product ions of interest are detected then said method further comprises:

halting the variation in the mass to charge ratios transmitted by the mass filter or otherwise operating the mass filter such that the mass to charge ratio, or range of mass to charge ratios, of the parent or precursor ions transmitted by the mass filter is static or remains constant for a first period of time; and then directing the parent or precursor ions transmitted by the mass filter during said first period of time into a fragmentation or reaction device operating in a second, different fragmentation or reaction mode of operation; and fragmenting or reacting the parent or precursor ions in the fragmentation or reaction device operating in the second fragmentation or reaction mode so as to produce second fragment or product ions.

By switching from a first fragmentation mode to a second fragmentation mode when an ion of interest is detected, the present invention enables a full un-biased MS/MS data set to be provided over a wide mass to charge ratio range with high-duty cycle, together with complementary detailed fragment data of interest, in a single experimental run or acquisition.

Said step of otherwise operating the mass filter may comprise stepping the mass to charge ratio, or range of mass to charge ratios, of the parent or precursor ions transmitted by the mass filter to a different value or range of values.

All of the steps of the method may be carried out during a single acquisition or experimental run.

The parent or precursor ions of interest may have a mass to charge ratio corresponding to the mass to charge ratio transmitted by the mass filter during said first period of time; and/or the first fragment or product ions of interest may be fragment or product ions of the same parent or precursor ions that are transmitted by the mass filter during said first period of time.

At the end of said first period of time, the method may resume the variation of the mass to charge ratios transmitted by the mass filter and may direct the parent or precursor ions transmitted by the mass filter into the fragmentation or reaction device operating in the first fragmentation or reaction mode so as to fragment or react these ions in the first fragmentation or reaction mode to produce first fragment or product ions.

The variation of the mass to charge ratios transmitted by the mass filter may be resumed until a further parent or precursor ion of interest and/or further first fragment or product ion of interest is detected, wherein the method may then halt again the variation in the mass to charge ratios transmitted by the mass filter or otherwise operate the mass filter such that the mass to charge ratio, or range of mass to charge ratios, of the parent or precursor ions transmitted by the mass filter is static or remains substantially constant for a second period of time; directs the parent or precursor ions transmitted by the mass filter during the second period of time into the fragmentation or reaction device operating in the second fragmentation or reaction mode; and fragments the parent or precursor ions in the fragmentation or reaction device operating in the second fragmentation or reaction mode so as to produce second fragment or product ions.

Alternatively, rather than directing the parent or precursor ions transmitted by the mass filter into the fragmentation or reaction device operating in the second fragmentation or reaction mode, the method may direct the parent or precursor ions transmitted by the mass filter into a fragmentation or reaction device operating in a third fragmentation or reaction mode so as to fragment or react these ions in a third, different fragmentation or reaction mode to produce third fragment or product ions.

Said further parent or precursor ions of interest may have a mass to charge ratio corresponding to the mass to charge ratio transmitted by the mass filter during said second period of time; and/or the further first fragment or product ions of interest may be fragment or product ions of the same further parent or precursor ions that are transmitted by the mass filter during said second period of time.

At the end of said second period of time, the method may resume the variation of the mass to charge ratios transmitted by the mass filter and may direct the parent or precursor ions transmitted by the mass filter into the fragmentation or reaction device operating in the first fragmentation or reaction mode so as to fragment or react these ions in the first fragmentation or reaction mode to produce first fragment or product ions.

The mass to charge ratio or mass to charge ratio range transmitted by the mass filter may be scanned continuously with time, except for said period(s) of time when said ions of interest have been detected. Alternatively, the mass to charge ratio or mass to charge ratio range of parent or precursor ions transmitted by the mass filter may be continually stepped with time, except for said period(s) of time when said ions of interest have been detected.

The mass to charge ratio and/or mass to charge ratio range of said parent or precursor ions transmitted into said fragmentation or reaction device operating in said second fragmentation or reaction mode of operation may correspond to the mass to charge ratio and/or mass to charge ratio range of said parent or precursor ions transmitted into said fragmentation or reaction device operating in said first fragmentation or reaction mode of operation.

Alternatively, the mass to charge ratio and/or mass to charge ratio range of parent or precursor ions transmitted into said fragmentation or reaction device operating in said second fragmentation or reaction mode of operation may be related to (i.e. based upon but not exactly corresponding to) the mass to charge ratio and/or mass to charge ratio range of parent or precursor ions transmitted into said fragmentation or reaction device operating in said first fragmentation or reaction mode of operation.

The mass to charge ratio and/or mass to charge ratio range of said parent or precursor ions transmitted into said fragmentation or reaction device operating in said second fragmentation or reaction mode of operation may be based upon a predicted or calculated mass to charge ratio and/or mass to charge ratio range of parent or precursor ions and/or fragment ions of interest.

From a second aspect the present invention provides a method of mass spectrometry comprising:

separating parent or precursor ions in an ion mobility separator;

transmitting the separated parent or precursor ions into a fragmentation or reaction device operating in a first fragmentation or reaction mode;

fragmenting or reacting the parent or precursor ions in the fragmentation or reaction device operating in the first fragmentation or reaction mode so as to produce first fragment or product ions;

wherein the ion mobility, or range of ion mobilities, of the parent or precursor ions transmitted by or from the ion mobility separator is varied with time such that parent or precursor ions of different ion mobilities are fragmented or reacted by the first fragmentation or reaction mode at different times;

monitoring for the detection of parent or precursor ions of interest and/or first fragment or product ions of interest, and wherein if parent or precursor ions of interest and/or first fragment or product ions of interest are detected then said method further comprises:

transmitting parent or precursor ions, said parent or precursor ions of interest, or parent or precursor ions of said first fragment or product ions of interest, into a fragmentation or reaction device operating in a second, different fragmentation or reaction mode of operation for a first period of time; and fragmenting or reacting the parent or precursor ions in the fragmentation or reaction device operating in the second fragmentation or reaction mode so as to produce second fragment or product ions.

The step of transmitting the ions into the fragmentation or reaction device operating in the second fragmentation or reaction mode of operation for the first period of time may correspond to transmitting only the parent or precursor ions of interest, or transmitting only the parent or precursor ions of said first fragment or product ions of interest, into the fragmentation or reaction device operating in the second mode of operation for the first period of time.

The step of transmitting the parent or precursor ions into the fragmentation or reaction device operating in the second mode of operation may comprise maintaining the ion mobility and/or ion mobility range of the parent or precursor ions transmitted by or from the ion mobility separator static or substantially constant for the first period of time.

At the end of said first period of time, the method may resume the variation of the ion mobilities transmitted by or from the ion mobility separator and direct the transmitted parent or precursor ions into the fragmentation or reaction device operating in the first fragmentation or reaction mode so as to fragment or react these ions in the first fragmentation or reaction mode to produce first fragment or product ions.

The variation of the ion mobilities transmitted may be resumed until a further parent or precursor ion of interest and/or further first fragment or product ion of interest is detected, wherein the method then halts the variation in the ion mobilities transmitted by or from the ion mobility separator or otherwise operates the spectrometer such that the ion mobility, or range of ion mobilities, of the parent or precursor ions transmitted by or from the ion mobility separator is static or remains substantially constant for a second period of time; directs the parent or precursor ions transmitted by or from the ion mobility separator during the second period of time into the fragmentation or reaction device operating in the second fragmentation or reaction mode; and fragments the parent or precursor ions in the fragmentation or reaction device operating in the second fragmentation or reaction mode so as to produce second fragment or product ions.

Alternatively, rather than directing the parent or precursor ions transmitted by or from the ion mobility separator into the fragmentation or reaction device operating in the second fragmentation or reaction mode, the method may direct the parent or precursor ions into a fragmentation or reaction device operating in a third fragmentation or reaction mode so as to fragment or react these ions in a third, different fragmentation or reaction mode to produce third fragment or product ions.

Said further parent or precursor ions of interest may have an ion mobility corresponding to the ion mobility transmitted by or from the ion mobility separator during said second period of time; and/or the further first fragment or product ions of interest may be fragment or product ions of the further parent or precursor ions transmitted during said second period of time.

At the end of said second period of time, the method may resume the variation of the ion mobilities transmitted by or from the ion mobility separator and may direct the transmitted parent or precursor ions into the fragmentation or reaction device operating in the first fragmentation or reaction mode so as to fragment or react these ions in the first fragmentation or reaction mode to produce first fragment or product ions.

The ion mobilities transmitted by or from the ion mobility separator may be scanned continuously with time, except for said period(s) of time when said ions of interest have been detected. Alternatively, the ion mobility or ion mobility range of parent or precursor ions transmitted by or from the ion mobility separator may be stepped continuously with time, except for said period(s) of time when said ions of interest have been detected.)

The parent or precursor ions of interest may have an ion mobility or range of ion mobilities corresponding to the ion mobility or range of ion mobilities transmitted into the fragmentation or reaction device operating in the second fragmentation or reaction mode of operation; and/or the first fragment or product ions of interest may be fragment or product ions of the same parent or precursor ions that are transmitted into the fragmentation or reaction device operating in the second fragmentation or reaction mode of operation.

The ion mobility and/or ion mobility range of said parent or precursor ions transmitted into said fragmentation or reaction device operating in said second fragmentation or reaction mode of operation may correspond to the ion mobility and/or ion mobility range of said parent or precursor ions transmitted into said first fragmentation or reaction device.

Alternatively, the ion mobility and/or ion mobility range of said parent or precursor ions transmitted into said fragmentation or reaction device operating in said second fragmentation or reaction mode of operation may be related to the ion mobility and/or ion mobility range of parent or precursor ions transmitted into said fragmentation or reaction device operating in said first fragmentation or reaction mode of operation.

The ion mobility and/or ion mobility range of said parent or precursor ions transmitted into said fragmentation or reaction device operating in said second fragmentation or reaction mode of operation may be based upon a predicted or calculated ion mobility and/or ion mobility range of parent or precursor and/or second fragment ions of interest.

It is recognised that the parent or precursor ions need not necessarily be mass filtered or separated by ion mobility prior to being fragmented or reacted.

Accordingly, from a third aspect the present invention provides a method of mass spectrometry comprising:

providing parent or precursor ions that are separated according to a physicochemical property;

transmitting the separated parent or precursor ions having different values of the physicochemical property into a fragmentation or reaction device operating in a first fragmentation or reaction mode at different times;

fragmenting or reacting the parent or precursor ions in the fragmentation or reaction device operating in the first fragmentation or reaction mode so as to produce first fragment or product ions;

monitoring for the detection of parent or precursor ions of interest and/or first fragment or product ions of interest, and wherein if parent or precursor ions of interest and/or first fragment or product ions of interest are detected then said method further comprises:

transmitting parent or precursor ions, the parent or precursor ions of interest, or parent or precursor ions of said first fragment or product ions of interest, into a fragmentation or reaction device operating in a second, different fragmentation or reaction mode of operation for a first time period; and fragmenting or reacting the parent or precursor ions in the fragmentation or reaction device operating in the second fragmentation or reaction mode during the first time period so as to produce second fragment or product ions.

The physicochemical property may be mass to charge ratio or ion mobility.

All of the steps may be carried out during a single acquisition or experimental run.

The step of providing parent or precursor ions that are separated according to a physicochemical property may comprise separating an analyte sample in a molecular separator and then ionising the sample eluting from the separator. For example, the separator may be a liquid or gas chromatography device.

The step of transmitting the ions into the fragmentation or reaction device operating in the second fragmentation or reaction mode of operation may correspond to transmitting only the parent or precursor ions of interest, or transmitting only the parent or precursor ions of said first fragment or product ions of interest, into the fragmentation or reaction device operating in the second mode of operation during the first period of time.

This may be achieved by mass filtering or ion mobility filtering the parent or precursor ions being transmitted to the fragmentation or reaction device operating in the second mode of operation.

At the end of said first period of time, the method may direct parent or precursor ions having different values of the physicochemical property into the fragmentation or reaction device operating in the first fragmentation or reaction mode so as to fragment or react these ions in the first fragmentation or reaction mode to produce first fragment or product ions.

It will be appreciated that the method according to the third aspect of the present invention may have any of the features described in relation to the first and second aspects of the present invention.

The methods disclosed herein may comprise fragmenting or reacting said parent or precursor ions in said first fragmentation or reaction mode and fragmenting or reacting said parent or precursor ions in said second fragmentation or reaction mode within the same fragmentation or reaction device. Alternatively, the methods may comprise fragmenting or reacting said parent or precursor ions in said first fragmentation or reaction mode in a first fragmentation or reaction device; and fragmenting or reacting said parent or precursor ions in said second fragmentation or reaction mode in a second different fragmentation or reaction device.

According to the methods disclosed herein, said first fragmentation mode of operation and/or said second fragmentation mode of operation may be selected from the group consisting of: (i) a Collisional Induced Dissociation ("CID") mode of operation; (ii) a Surface Induced Dissociation ("SID") mode of operation; (iii) an Electron Transfer Dissociation ("ETD") mode of operation; (iv) an Electron Capture Dissociation ("ECD") mode of operation; (v) an Electron Collision or Impact Dissociation mode of operation; (vi) a Photo Induced Dissociation ("PID") mode of operation; (vii) a Laser Induced Dissociation mode of operation; (viii) an infrared radiation induced dissociation mode of operation; (ix) an ultraviolet radiation induced dissociation mode of operation; (x) a nozzle-skimmer interface fragmentation mode of operation; (xi) an in-source fragmentation mode of operation; (xii) an in-source Collision Induced Dissociation mode of operation; (xiii) a thermal fragmentation mode of operation; (xiv) an electric field induced fragmentation mode of operation; (xv) a magnetic field induced fragmentation mode of operation; (xvi) an enzyme digestion or enzyme degradation fragmentation mode of operation; (xvii) an ion-ion reaction fragmentation mode of operation; (xviii) an ion-molecule reaction fragmentation mode of operation; (xix) an ion-atom reaction fragmentation mode of operation; (xx) an ion-metastable ion reaction fragmentation mode of operation; (xxi) an ion-metastable molecule reaction fragmentation mode of operation; (xxii) an ion-metastable atom reaction fragmentation mode of operation; (xxiii) an ion-ion reaction mode of operation wherein ions react to form adduct or product ions; (xxiv) an ion-molecule reaction mode of operation wherein ions react to form adduct or product ions; (xxv) an ion-atom reaction mode of operation wherein ions react to form adduct or product ions; (xxvi) an ion-metastable ion reaction mode of operation wherein ions react to form adduct or product ions; (xxvii) an ion-metastable molecule reaction mode of operation wherein ions react to form adduct or product ions; (xxviii) an ion-metastable atom reaction mode of operation wherein ions react to form adduct or product ions; and (xxix) an Electron Ionisation Dissociation ("EID") mode of operation.

According to the methods disclosed herein, the first fragmentation or reaction mode of operation may comprise a Collisional Induced Dissociation ("CID") mode of operation; and/or the second fragmentation or reaction mode of operation may comprise an Electron Transfer Dissociation ("ETD") mode of operation.

According to the methods disclosed herein, the rate of charge of the parent or precursor ions entering the fragmentation or reaction device operating in the first fragmentation or reaction mode may be a first rate, and the rate of charge of the parent or precursor ions entering the fragmentation or reaction device operating in the second fragmentation or reaction mode may be a second, lower rate.

According to the methods disclosed herein, the step of fragmenting or reacting the parent or precursor ions in the fragmentation or reaction device operating in the second fragmentation or reaction mode may be performed immediately after detecting the parent or precursor ions and/or fragment or product ions of interest, or after a period of time but during the same acquisition or experimental run.

The methods disclosed herein may comprise mass analysing and detecting said parent or precursor ions and/or said first fragment or product ions produced in the first mode of operation; and/or mass analysing and detecting said second fragment or product ions produced in the second mode of operation.

The methods disclosed herein may comprise mass analysing the ions using a Time of Flight mass analyser.

The method may comprise identifying or quantifying an analyte from the first and/or second fragment or product ions detected.

The methods disclosed herein may comprise passing said parent or precursor ions and/or said fragment ions through an ion mobility spectrometer prior to mass analysing and detecting said parent or precursor ions and/or said fragment ions.

According to the methods disclosed herein, any one of the fragmentation or reaction devices may be repeatedly switched between high fragmentation or reaction mode in which the parent or precursor ions are fragmented and a low fragmentation or reaction mode in which substantially fewer parent or precursor ions are fragmented.

The methods disclosed herein may comprise the step of repeatedly switching between a mode of operation in which said parent or precursor ions are passed into any one of the fragmentation or reaction devices described and are fragmented or reacted, and another mode of operation in which said parent or precursor ions bypass such fragmentation or reaction device.

According to the methods disclosed herein, said step of monitoring for the detection of parent or precursor ions of interest may comprise monitoring for neutral loss ions of interest.

All of the steps of the method described herein may be performed in a single acquisition or experimental run.

According to a fourth aspect the present invention provides a method of mass spectrometry comprising:

fragmenting or reacting parent or precursor ions having a first mass to charge ratio range in a fragmentation or reaction device operating in a first fragmentation or reaction mode so as to produce first fragment or product ions;

monitoring for parent or precursor ions and/or first fragment or product ions of interest;

wherein if parent or precursor ions and/or first fragment or product ions of interest are detected then said method further comprises:

fragmenting or reacting parent or precursor ions having a second, smaller mass to charge ratio range in a fragmentation or reaction device operating in a second fragmentation or reaction mode so as to produce second fragment or product ions.

The fourth aspect of the present invention may have any of the features described herein in relation to the first, second or third aspects of the present invention.

The first fragmentation or reaction mode of operation may comprise a Collisional Induced Dissociation ("CID") mode of operation; and/or the second fragmentation or reaction mode of operation may comprise an Electron Transfer Dissociation ("ETD") mode of operation.

However, it is contemplated that the first fragmentation mode of operation and/or said second fragmentation mode of operation may be selected from the group consisting of: (i) a Collisional Induced Dissociation ("CID") mode of operation; (ii) a Surface Induced Dissociation ("SID") mode of operation; (iii) an Electron Transfer Dissociation ("ETD") mode of operation; (iv) an Electron Capture Dissociation ("ECD") mode of operation; (v) an Electron Collision or Impact Dissociation mode of operation; (vi) a Photo Induced Dissociation ("PID") mode of operation; (vii) a Laser Induced Dissociation mode of operation; (viii) an infrared radiation induced dissociation mode of operation; (ix) an ultraviolet radiation induced dissociation mode of operation; (x) a nozzle-skimmer interface fragmentation mode of operation; (xi) an in-source fragmentation mode of operation; (xii) an in-source Collision Induced Dissociation mode of operation; (xiii) a thermal fragmentation mode of operation; (xiv) an electric field induced fragmentation mode of operation; (xv) a magnetic field induced fragmentation mode of operation; (xvi) an enzyme digestion or enzyme degradation fragmentation mode of operation; (xvii) an ion-ion reaction fragmentation mode of operation; (xviii) an ion-molecule reaction fragmentation mode of operation; (xix) an ion-atom reaction fragmentation mode of operation; (xx) an ion-metastable ion reaction fragmentation mode of operation; (xxi) an ion-metastable molecule reaction fragmentation mode of operation; (xxii) an ion-metastable atom reaction fragmentation mode of operation; (xxiii) an ion-ion reaction mode of operation wherein ions react to form adduct or product ions; (xxiv) an ion-molecule reaction mode of operation wherein ions react to form adduct or product ions; (xxv) an ion-atom reaction mode of operation wherein ions react to form adduct or product ions; (xxvi) an ion-metastable ion reaction mode of operation wherein ions react to form adduct or product ions; (xxvii) an ion-metastable molecule reaction mode of operation wherein ions react to form adduct or product ions; (xxviii) an ion-metastable atom reaction mode of operation wherein ions react to form adduct or product ions; and (xxix) an Electron Ionisation Dissociation ("EID") mode of operation.

The rate of charge of the parent or precursor ions entering the fragmentation or reaction device operating in the first fragmentation or reaction mode may be a first rate, and the rate of charge of the parent or precursor ions entering the fragmentation or reaction device operating in the second fragmentation or reaction mode may be a second, lower rate.

The method may comprise fragmenting or reacting said parent or precursor ions in said first fragmentation or reaction mode and fragmenting or reacting said parent or precursor ions in said second fragmentation or reaction mode within the same fragmentation or reaction device. Alternatively, the methods may comprise fragmenting or reacting said parent or precursor ions in said first fragmentation or reaction mode in a first fragmentation or reaction device; and fragmenting or reacting said parent or precursor ions in said second fragmentation or reaction mode in a second different fragmentation or reaction device.

The parent or precursor ions of interest may have a mass to charge ratio corresponding to the mass to charge ratio(s) transmitted into said fragmentation or reaction device operating in a second fragmentation or reaction mode; and/or the first fragment or product ions of interest may be fragment or product ions of the same parent or precursor ions that are transmitted into said fragmentation or reaction device operating in a second fragmentation or reaction mode.

The step of transmitting the ions into the fragmentation or reaction device operating in the second fragmentation or reaction mode of operation may correspond to transmitting only the parent or precursor ions of interest, or transmitting only the parent or precursor ions of said first fragment or product ions of interest, into the fragmentation or reaction device operating in the second mode of operation for the first period of time.

This may be achieved by mass filtering or ion mobility filtering the parent or precursor ions being transmitted to the fragmentation or reaction device operating in the second mode of operation.

The step of fragmenting or reacting the parent or precursor ions in the fragmentation or reaction device operating in the second fragmentation or reaction mode may be performed immediately after detecting the parent or precursor ions and/or fragment or product ions of interest, or after a period of time but during the same acquisition or experimental run.

The method may comprise mass analysing and detecting said parent or precursor ions and/or said first fragment or product ions produced in the first mode of operation; and/or mass analysing and detecting said second fragment or product ions produced in the second mode of operation.

The methods disclosed herein may comprise mass analysing the ions using a Time of Flight mass analyser.

The method may comprise identifying or quantifying an analyte from the first and/or second fragment or product ions detected.

The method may comprise passing said parent or precursor ions and/or said fragment ions through an ion mobility spectrometer prior to mass analysing and detecting said parent or precursor ions and/or said fragment ions.

Any one of the fragmentation or reaction devices may be repeatedly switched between high fragmentation or reaction mode in which the parent or precursor ions are fragmented and a low fragmentation or reaction mode in which substantially fewer parent or precursor ions are fragmented.

The method may comprise the step of repeatedly switching between a mode of operation in which said parent or precursor ions are passed into any one of the fragmentation or reaction devices described and are fragmented or reacted, and another mode of operation in which said parent or precursor ions bypass such fragmentation or reaction device.

The step of monitoring for the detection of parent or precursor ions of interest may comprise monitoring for neutral loss ions of interest.

The parent or precursor ions of interest and/or first fragment or product ions of interest described herein may be ions having a target mass to charge ratio or range of target mass to charge ratios.

The may comprise separating the parent or precursor ions according to their ion mobility; and the parent or precursor ions of interest may be ions having a target ion mobility or collisional cross section, or a target range of ion mobilities or collisional cross sections; and/or the first fragment or product ions of interest may be ions derived from parent or precursor ions having a target ion mobility or collisional cross section, or a target range of ion mobilities or collisional cross sections.

All of the steps of the method described above may be performed in a single acquisition or experimental run.

The present invention also provides a mass spectrometer arranged and configured to perform any of the methods described herein.

Accordingly, from the first aspect the present invention provides a mass spectrometer comprising:
a mass filter;
at least one fragmentation or reaction device;
a mass analyser; and
a control system arranged and adapted to:
mass filter parent or precursor ions in the mass filter;
transmit the mass filtered parent or precursor ions into one of said at least one fragmentation or reaction devices;
operate said one fragmentation or reaction device in a first fragmentation or reaction mode so as to fragment or react the parent or precursor ions and produce first fragment or product ions;
vary the mass to charge ratio, or range of mass to charge ratios, of the parent or precursor ions transmitted by the mass filter with time such that parent or precursor ions of different mass to charge ratios are fragmented or reacted by the first fragmentation or reaction mode at different times;
monitor for the detection of parent or precursor ions of interest and/or first fragment or product ions of interest, and upon detection of parent or precursor ions of interest and/or first fragment or product ions of interest then said control system is arranged and adapted to:
halt the variation in the mass to charge ratios transmitted by the mass filter or otherwise operate the mass filter such that the mass to charge ratio, or range of mass to charge ratios, of the parent or precursor ions transmitted by the mass filter is static or remains constant for a first period of time; and
direct the parent or precursor ions transmitted by the mass filter during said first period of time into one of said at least one fragmentation or reaction devices; and
operate the fragmentation or reaction device in a second fragmentation or reaction mode so as to fragment or react the parent or precursor ions and produce second fragment or product ions.

From the second aspect the present invention provides a mass spectrometer comprising:
an ion mobility separator;
at least one fragmentation or reaction device;
a mass analyser; and
a control system arranged and adapted to:
separate parent or precursor ions in the ion mobility separator;
transmit the separated parent or precursor ions into one of said fragmentation or reaction devices;
operate the fragmentation or reaction device in a first fragmentation or reaction mode so as to fragment or react the parent or precursor ions and produce first fragment or product ions;
vary the ion mobility, or range of ion mobilities, of the parent or precursor ions transmitted by or from the ion mobility separator with time such that parent or precursor ions of different ion mobilities are fragmented or reacted by the first fragmentation or reaction mode at different times;
monitor for the detection of parent or precursor ions of interest and/or first fragment or product ions of interest, and upon detection of parent or precursor ions of interest and/or first fragment or product ions of interest then said control system is arranged and adapted to:
transmit parent or precursor ions, said parent or precursor ions of interest, or parent or precursor ions of said first fragment or product ions of interest, into one of said at least one fragmentation or reaction devices; and
operate the fragmentation or reaction device in a second fragmentation or reaction mode so as to fragment or react the parent or precursor ions and produce second fragment or product ions.

From the third aspect the present invention provides a mass spectrometer comprising:
a source of ions for providing parent or precursor ions that are separated according to a physicochemical property;
at least one fragmentation or reaction device;
a mass analyser; and
a control system arranged and adapted to:
transmit parent or precursor ions having different values of the physicochemical property from said source into one of said fragmentation or reaction devices at different times;
operate the fragmentation or reaction device in a first fragmentation or reaction mode so as to fragment or react the parent or precursor ions and produce first fragment or product ions;
monitor for the detection of parent or precursor ions of interest and/or first fragment or product ions of interest, and upon detection of parent or precursor ions of interest and/or first fragment or product ions of interest then said control system is arranged and adapted to:
transmit parent or precursor ions, said parent or precursor ions of interest, or parent or precursor ions of said first fragment or product ions of interest, into one of said at least one fragmentation or reaction devices; and
operate the fragmentation or reaction device in a second fragmentation or reaction mode so as to fragment or react the parent or precursor ions and produce second fragment or product ions.

From the fourth aspect the present invention provides a mass spectrometer comprising:
at least one fragmentation or reaction device;
a mass analyser; and a control system arranged and adapted to:

transmit parent or precursor ions having a first mass to charge ratio range to one of the fragmentation or reaction devices;

operate the fragmentation or reaction device in a first fragmentation or reaction mode so as to fragment or react the parent or precursor ions and produce first fragment or product ions;

monitor for the detection of parent or precursor ions of interest and/or first fragment or product ions of interest, and upon detection of parent or precursor ions of interest and/or first fragment or product ions of interest then said control system is arranged and adapted to:

transmit parent or precursor ions having a second, smaller mass to charge ratio range to one of the fragmentation or reaction devices; and operate the fragmentation or reaction device in a second fragmentation or reaction mode so as to fragment or react the parent or precursor ions and produce second fragment or product ions.

According to another aspect of the present invention there is provided a method of mass spectrometry comprising:

(i) fragmenting parent or precursor ions in a fragmentation or reaction device operating in a first fragmentation mode of operation so as to produce first fragment ions;

(ii) mass analysing and detecting the parent or precursor ions and/or the first fragment ions; and (iii) monitoring for parent or precursor ions and/or first fragment ions of interest;

wherein if parent or precursor ions and/or first fragment ions of interest are detected then the method further comprises:

(iv) fragmenting parent or precursor ions in a fragmentation or reaction device operating in a second different fragmentation mode of operation so as to produce second fragment ions.

Parent or precursor ions may be fragmented in a fragmentation or reaction device operating in a first fragmentation mode of operation, such as in a Collision Induced Dissociation mode of operation, so as to produce fragment ions.

The parent or precursor ions and/or the fragment ions may be mass analysed and detected using an orthogonal acceleration Time of Flight mass analyser. The data from the Time of Flight mass analyser may be monitored for the appearance of parent or precursor ions, neutral loss ions or fragment ions of interest. If ions of interest are detected then the system may switch to fragmenting parent or precursor ions using a second different fragmentation mode of operation, such as Electron Transfer Dissociation, so as to produce second fragment ions.

The system may be configured so as to switch from the first fragmentation mode of operation into the second fragmentation mode of operation when particular parent or precursor ions, neutral loss ions or fragment ions are detected in the data obtained during the first fragmentation mode of operation that are indicative that it might be useful or of interest to obtain data using the second fragmentation mode of operation.

For example, where the first and second fragmentation modes of operation are Collision Induced Dissociation and Electron Transfer Dissociation respectively, as discussed above, Collision Induced Dissociation is particularly suited for fragmenting parent or precursor ions over a wide mass to charge ratio range, but limited in the types of fragmentation that it can induce, particularly in the analysis of post translationally modified peptides. In contrast, Electron Transfer Dissociation is ill-suited for fragmenting parent or precursor ions over a wide mass to charge ratio range, but can induce different types of fragmentation which are particularly useful in the analysis of post translationally modified peptides. Furthermore, certain fragment ions that can be induced by Collision Induced Dissociation may be indicative that a particular modification is present i.e. may be indicative that it would be useful or of interest to further obtain Electron Transfer Dissociation data. One example is oxonium ions generated from glycosylated peptides. Accordingly, the system may be configured so as to switch to an Electron Transfer Dissociation fragmentation mode of operation when oxonium ions are detected in Collision Induced Dissociation mass spectral data.

Whilst data is being acquired in the first fragmentation mode of operation, the mass to charge ratio range of parent or precursor ions that are being transmitted into the fragmentation device may be scanned or stepped with time (e.g. by mass filtering the parent or precursor ions).

It is desirable for the first fragmentation mode of operation to be suitable for fragmenting parent or precursor ions over a wide mass to charge ratio range. Whilst data is being acquired in the second fragmentation mode of operation, the mass to charge ratio range of ions transmitted into the fragmentation device may be held substantially constant. In this way, the second fragmentation mode of operation need not be suitable for fragmenting parent or precursor ions over a wide mass to charge ratio range.

After acquiring sufficient data in the second fragmentation mode of operation, the system may be configured to switch back to the first fragmentation mode of operation and to continue to scan or step the mass to charge ratio range of parent or precursor ions that are transmitted into the fragmentation device.

It will therefore be apparent that the methods enable a full un-biased MS/MS data set to be provided over a wide mass to charge ratio range with high-duty cycle, together with complementary detailed fragment data of interest, in a single experimental run or acquisition.

Complementary and specific Electron Transfer Dissociation data can be provided during a data independent two dimensional MS/MS Collision Induced Dissociation experiment.

The method may comprise fragmenting the parent or precursor ions so as to produce the first fragment ions and fragmenting the parent or precursor ions so as to produce the second fragment ions in the same fragmentation or reaction device, wherein the fragmentation or reaction device is arranged and adapted to be operable in the first fragmentation mode of operation and the second different fragmentation mode of operation.

Alternatively, the method may further comprise: fragmenting the parent or precursor ions in a first fragmentation or reaction device so as to produce the first fragment ions, wherein the first fragmentation or reaction device is arranged and adapted to be operable in the first fragmentation mode of operation; and fragmenting the parent or precursor ions in a second different fragmentation or reaction device so as to produce the second fragment ions wherein the second fragmentation or reaction device is arranged and adapted to be operable in the second fragmentation mode of operation.

The first fragmentation mode of operation and/or the second fragmentation mode of operation may be selected from the group consisting of: (i) a Collisional Induced Dissociation ("CID") mode of operation; (ii) a Surface Induced Dissociation ("SID") mode of operation; (iii) an Electron Transfer Dissociation ("ETD") mode of operation; (iv) an Electron Capture Dissociation ("ECD") mode of operation; (v) an Electron Collision or Impact Dissociation mode of operation; (vi) a Photo Induced Dissociation ("PID") mode of operation; (vii) a Laser Induced Dissociation mode of operation; (viii) an infrared radiation induced dissociation mode of operation; (ix) an ultraviolet radiation induced dissociation mode of operation; (x) a nozzle-skimmer interface fragmentation mode of operation; (xi) an in-source fragmentation mode of operation; (xii) an in-source Collision Induced Dissociation mode of operation; (xiii) a thermal fragmentation mode of operation; (xiv) an electric field induced fragmentation mode of operation; (xv) a magnetic field induced fragmentation mode of operation; (xvi) an enzyme digestion or enzyme degradation fragmentation mode of operation; (xvii) an ion-ion reaction fragmentation mode of operation; (xviii) an ion-molecule reaction fragmentation mode of operation; (xix) an ion-atom reaction fragmentation mode of operation; (xx) an ion-metastable ion reaction fragmentation mode of operation; (xxi) an ion-metastable molecule reaction fragmentation mode of operation; (xxii) an ion-metastable atom reaction fragmentation mode of operation; (xxiii) an ion-ion reaction mode of operation wherein ions react to form adduct or product ions; (xxiv) an ion-molecule reaction mode of operation wherein ions react to form adduct or product ions; (xxv) an ion-atom reaction mode of operation wherein ions react to form adduct or product ions; (xxvi) an ion-metastable ion reaction mode of operation wherein ions react to form adduct or product ions; (xxvii) an ion-metastable molecule reaction mode of operation wherein ions react to form adduct or product ions; (xxviii) an ion-metastable atom reaction mode of operation wherein ions react to form adduct or product ions; and (xxix) an Electron Ionisation Dissociation ("EID") mode of operation.

The first fragmentation mode of operation may comprise a Collisional Induced Dissociation ("CID") mode of operation and/or the second fragmentation mode of operation may comprise an Electron Transfer Dissociation ("ETD") mode of operation.

The method may further comprise mass filtering parent or precursor ions prior to transmitting the parent or precursor ions into the fragmentation or reaction device operating in the first fragmentation mode of operation, such that the mass to charge ratio and/or mass to charge ratio range of the transmitted parent or precursor ions varies with time.

The mass to charge ratio and/or mass to charge ratio range of the transmitted parent or precursor ions may be scanned continuously with time or stepped with time.

If the parent or precursor and/or first fragment ions of interest are detected then the method may further comprise mass filtering parent or precursor ions prior to transmitting the parent or precursor ions into the fragmentation or reaction device operating in the second fragmentation mode of operation such that the mass to charge ratio and/or mass to charge ratio range of the transmitted parent or precursor ions is static or remains substantially constant for a period of time.

The mass to charge ratio and/or mass to charge ratio range of the parent or precursor ions transmitted into the fragmentation or reaction device operating in the second fragmentation mode of operation may correspond to the mass to charge ratio and/or mass to charge ratio range of the parent or precursor ions transmitted into the fragmentation or reaction device operating in the first fragmentation mode of operation.

Alternatively, the mass to charge ratio and/or mass to charge ratio range of the parent or precursor ions transmitted into the fragmentation or reaction device operating in the second fragmentation mode of operation may be related to (i.e. based upon but not corresponding exactly to) the mass to charge ratio and/or mass to charge ratio range of the parent or precursor ions transmitted into the fragmentation or reaction device operating in the first fragmentation mode of operation.

For example, the mass to charge ratio and/or mass to charge ratio range of the parent or precursor ions transmitted into the fragmentation or reaction device operating in the second fragmentation mode of operation may be based upon a predicted or calculated mass to charge ratio and/or mass to charge ratio range of parent or precursor ions and/or fragment ions of interest.

According to an embodiment, the method may further comprise passing the parent or precursor ions through an ion mobility spectrometer prior to transmitting the parent or precursor ions into the fragmentation or reaction device operating in the first fragmentation mode of operation, such that the ion mobility and/or ion mobility range of the transmitted parent or precursor ions varies with time.

The ion mobility and/or ion mobility range of the parent or precursor ions transmitted into the fragmentation or reaction device operating in the first fragmentation mode of operation may be scanned continuously or arranged otherwise to vary continuously with time or may be stepped with time.

If parent or precursor ions and/or first fragment ions of interest are detected then the method may further comprise passing parent or precursor ions through an ion mobility spectrometer prior to transmitting the parent or precursor ions into the fragmentation or reaction device operating in the second fragmentation mode of operation, such that the ion mobility and/or ion mobility range of the transmitted parent or precursor ions is static or remains substantially constant for a period of time.

The ion mobility and/or ion mobility range of the parent or precursor ions transmitted into the fragmentation or reaction device operating in the second fragmentation mode of operation may correspond to the ion mobility and/or ion mobility range of the parent or precursor ions transmitted into the first fragmentation or reaction device.

Alternatively, the ion mobility and/or ion mobility range of the parent or precursor ions transmitted into the fragmentation or reaction device operating in the second fragmentation mode of operation may be related to (i.e. based upon but not corresponding exactly to) the ion mobility and/or ion mobility range of the parent or precursor ions transmitted into the fragmentation or reaction device operating in the first fragmentation mode of operation.

For example, the ion mobility and/or ion mobility range of the parent or precursor ions transmitted into the fragmentation or reaction device operating in the second fragmentation mode of operation may be based upon a predicted or calculated ion mobility and/or ion mobility range of parent or precursor ions and/or second fragment ions of interest.

According to another aspect of the present invention there is provided a method of mass spectrometry comprising:

(i) fragmenting parent or precursor ions having a first mass to charge ratio range in a fragmentation or reaction device so as to produce first fragment ions;

(ii) mass analysing and detecting the parent or precursor ions and/or the first fragment ions; and (iii) monitoring for parent or precursor ions and/or first fragment ions of interest;

wherein if parent or precursor ions and/or first fragment ions of interest are detected then the method further comprises:

(iv) fragmenting parent or precursor ions having a second mass to charge ratio range so as to produce second fragment ions, wherein the second mass to charge ratio range is smaller than the first mass to charge ratio range.

The fragmentation or reaction device may be selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The fragmentation or reaction device may comprise an Electron Transfer Dissociation ("ETD") fragmentation device.

The method may further comprise carrying out step (iv) after detecting parent or precursor ions and/or fragment ions of interest, either: immediately; or after a period of time, and during the same acquisition or experimental run.

The method may further comprise: (v) mass analysing and detecting the parent or precursor ions and/or the second fragment ions.

The method may further comprise returning to step (i) after step (v).

Steps (i)-(v) may be carried out in a single acquisition or experimental run.

The method may further comprise repeatedly switching the fragmentation or reaction device between a first mode of operation in which the parent or precursor ions are fragmented and a second mode of operation in which substantially fewer parent or precursor ions are fragmented.

The method may further comprise repeatedly switching between a mode of operation in which the parent or precursor ions are passed into the fragmentation or reaction device and are fragmented and a mode of operation in which the parent or precursor ions bypass the fragmentation or reaction device.

The method may further comprise mass analysing the ions using a Time of Flight mass analyser.

The method may further comprise passing the parent or precursor ions and/or the fragment ions through an ion mobility spectrometer prior to mass analysing and detecting the parent or precursor ions and/or the fragment ions.

Step (iii) may comprise monitoring for neutral loss ions of interest.

Steps (i)-(iii) may comprise a Data Independent Acquisition ("DIA") mode of operation and/or step (iv) may comprise a Data Dependent Acquisition ("DDA") mode of operation.

According to another aspect of the present invention there is provided a mass spectrometer comprising:
    one or more fragmentation or reaction devices;
    a mass analyser arranged downstream of the one or more fragmentation or reaction devices; and
    a control system arranged and adapted:
    (i) to cause parent or precursor ions to be fragmented in one of the one or more fragmentation or reaction devices operating in a first fragmentation mode of operation so as to produce first fragment ions;
    (ii) to mass analyse and detect the parent or precursor ions and/or the first fragment ions; and
    (iii) to monitor for parent or precursor ions and/or first fragment ions of interest;
    wherein if parent or precursor ions and/or first fragment ions of interest are detected then the control system is further arranged and adapted:
    (iv) to cause parent or precursor ions to be fragmented in one of the one or more fragmentation or reaction devices operating in a second fragmentation mode of operation so as to produce second fragment ions.

According to another aspect of the present invention there is provided a mass spectrometer comprising:
    a fragmentation or reaction device;
    a mass analyser arranged downstream of the fragmentation or reaction device; and
    a control system arranged and adapted:
    (i) to cause parent or precursor ions having a first mass to charge ratio range to be fragmented in the fragmentation or reaction device so as to produce first fragment ions;
    (ii) to mass analyse and detect the parent or precursor ions and/or the first fragment ions; and
    (iii) to monitor for parent or precursor ions and/or first fragment ions of interest;
    wherein if parent or precursor ions and/or first fragment ions of interest are detected then the control system is further arranged and adapted:
    (iv) to cause parent or precursor ions having a second mass to charge ratio range to be fragmented so as to produce second fragment ions, wherein the second mass to charge ratio range is smaller than the first mass to charge ratio range.

The mass spectrometer disclosed herein may comprise:
    (a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

BRIEF DESCRIPTION OF THE DRAWINGS

Various embodiments of the present invention will now be described, by way of example only, and with reference to the accompanying drawings in which:

FIG. 2A illustrates a parent ion mass spectrum of substance P, FIG. 2B shows a corresponding ETD fragmentation mass spectrum obtained by subjecting triply charged substance P parent ions having a mass to charge ratio of 450 to Electron Transfer Dissociation fragmentation.

DETAILED DESCRIPTION OF PREFERRED EMBODIMENT

Figure 1A:
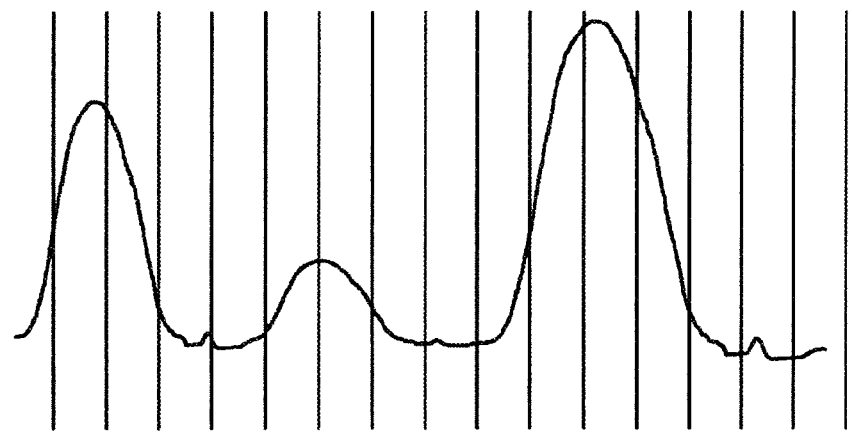
FIG. 1 diagrammatically illustrates a method wherein parent ion or Collisional Induced Dissociation fragmentation mass spectral data is obtained and the mass spectrometer is then switched to acquire Electron Transfer Dissociation fragmentation data if parent or fragment ions of interest are observed.

It will be understood that Data Independent Acquisitions can be advantageous compared with Data Dependent Acquisition methods which are triggered by a full survey scan since Data Independent Acquisitions collect unbiased MS/MS data on all ions present. Known Data Independent Acquisition methods typically use a Collision Induced Dissociation fragmentation cell in order to fragment parent or precursor ions so as to produce fragment ions. However, fragmenting ions using a Collision Induced Dissociation fragmentation cell suffers from certain limitations especially for the analysis of post translationally modified peptides where little information is attained using Collision Induced Dissociation other than the loss of the side chain. However, certain Collision Induced Dissociation fragment ions can still indicate that a particular modification is present such as the oxonium ions generated from glycosylated peptides.

According to methods of the present invention, a subsequent Data Dependent Acquisition MS/MS analysis may be performed on particular ions of interest during the same run. This approach allows experiments to be performed which are able to selectively mine deeper into the sample and perform more detailed and focused experiments, e.g. Electron Transfer Dissociation experiments.

Electron Transfer Dissociation is particularly useful for mining post translational modifications ("PTMs") such as glycosylation, O-GlcNac and sulfonation etc. Unfortunately, the performance of Data Independent Acquisition methods (in which parent or precursor ions having a wide mass to charge ratio range are fragmented) using Electron Transfer Dissociation (rather than Collision Induced Dissociation) is curtailed by the excessive amount of charge flowing through the Electron Transfer Dissociation reaction cell. It will be understood that there has to be a surplus of reagent anions available to react with analyte cation charges otherwise the analyte cation charges will tend to neutralise the anions rendering the Electron Transfer Dissociation reaction unviable.

According to the methods of the present invention, a mass filter may be arranged upstream of an ion mobility spectrometer or separator ("IMS") and an orthogonal acceleration Time of Flight ("oa-ToF") mass spectrometer may be arranged downstream of the ion mobility spectrometer or separator. However, it is not essential that an ion mobility spectrometer or separator is provided and hence according to embodiments a mass filter may be arranged upstream of an orthogonal acceleration Time of Flight mass analyser without an ion mobility spectrometer or separator necessarily being provided.

The mass filter is preferably arranged or is otherwise programmed to scan the mass to charge ratio of ions that it transmits (or to jump between discrete mass to charge ratio windows) across all theoretical ions or across a relatively wide range of mass to charge ratios. When an ion peak of interest (or a specific Collision Induced Dissociation product ion or fragment ion of interest or other fragment or product ion of interest) is detected by the Time of Flight mass analyser system, the mass filter is preferably temporarily programmed to stay at or jump to the mass to charge ratio window of interest whilst the corresponding parent or precursor ions undergo or are subjected to Electron Transfer Dissociation fragmentation.

Thus, the methods of the present invention may enable a semi-targeted hybrid acquisition mode of operation to be performed that combines the benefits of two dimensional MS/MS and fragment/product ion triggered Data Dependent Acquisition.

The mass spectrometer may initially be operated in a Data Independent Acquisition mode and the mass spectrometer may then be switched into an Electron Transfer Dissociation fragmentation mode of operation in which the mass to charge ratio range of parent or precursor ions of interest transmitted by a mass filter is preferably sequentially incremented.

A particular advantage of these methods is that during the Electron Transfer Dissociation mode of operation significantly less parent or precursor charge flows through the Electron Transfer Dissociation reaction cell than would otherwise occur if the range of mass to charge ratios were not restricted. The reduced amount of charge flowing through the Electron Transfer Dissociation reaction cell allows effective or optimal Electron Transfer Dissociation fragmentation to occur.

The decision to switch the mass spectrometer so as to operate in an Electron Transfer Dissociation mode of operation may be made based upon real-time Data Independent Acquisition MS/MS data.

A control system may be arranged to recognise a specific targeted parent or precursor ion, a neutral loss ion of interest or the appearance of e.g. oxonium or other ions indicating the arrival of a parent or precursor ion of interest or a fragment ion of interest.

The Electron Transfer Dissociation acquisitions may last for tens of milliseconds, wherein after this period of time the instrument may then jumps back into a Data Independent Acquisition mode of operation and preferably continues to collect data.

Figure 1B:
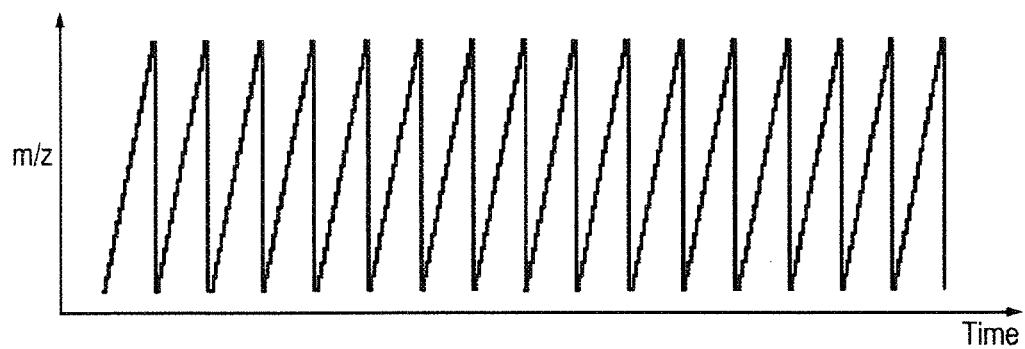
Figure 1C:
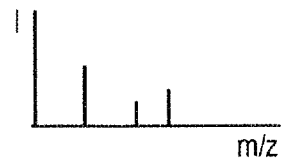
Figure 1D:

FIG. 1A diagrammatically illustrates an embodiment of the present invention wherein a sample elutes from a liquid chromatography device and is then ionised so as to form parent ions. The ion signal as a function of time is shown. A mass filter is provided downstream for mass filtering the parent ions prior to transmitting them to a CID fragmentation cell. The mass to charge ratio transmittal window of the mass filter is scanned with time, as shown in FIG. 1B, such that the mass to charge ratios of the ions fragmented by CID varies with time. The fragment ions are detected and when a fragment ion of interest (or parent ion of interest) is detected, as shown by the spectrum in FIG. 1C, the scanning of the mass to charge ratios transmitted by the mass filter is paused for a period of time. During this period of time, the parent ions are transmitted to an ETD fragmentation device so as to form ETD fragment ions, as shown by the spectrum in FIG. 1D. At the end of the period of time, the scanning of the mass filter is resumed until another parent ion or fragment ion of interest is detected. This process may be repeated over and over during a single acquisition (i.e. a single experimental run of a single sample). CID fragment ions and ETD fragment ions may be correlated to a parent ion and, for example, used to identify the parent ion.

FIG. 2A shows parent ion data which was obtained by analysing an infusion of substance-P using a mass spectrometer according the present invention. The mass spectrometer was configured to obtain mass spectral data wherein the mass transmission window of a mass filter was progressively scanned in steps. The mass spectrometer was arranged to perform 5 scans/sec with a 0.1 s scan time, a 0.1 s refill and interval time and an interscan delay time of 0.01 s. Parent ion mass spectral data was obtained for ions having mass to charge ratios between 440 and 460. WATERS® Research Enabled Software ("WRENS") was used to obtain parent or precursor ion data wherein a mass filter was programmed to jump at 2 Da intervals. Precursor or parent ions of interest were then subjected to Electron Transfer Dissociation.

FIG. 2B shows Electron Transfer Dissociation fragmentation data obtained by subjecting parent or precursor ions having a mass to charge ratio of 450 as identified from the data shown in FIG. 2A to Electron Transfer Dissociation fragmentation.

Figure 2C:
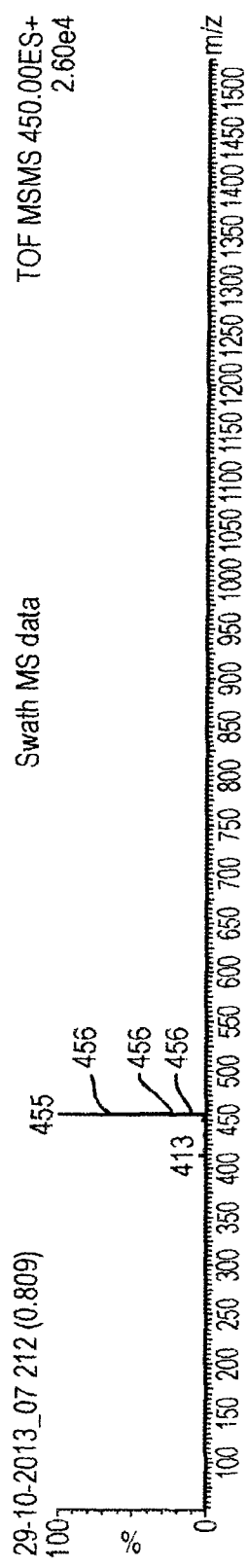
FIG. 2C shows a parent ion mass spectrum of an adduct of substance P.

FIG. 2C shows mass spectral data showing a different parent or precursor ion corresponding to a Na adduct ion.

Figure 2D:
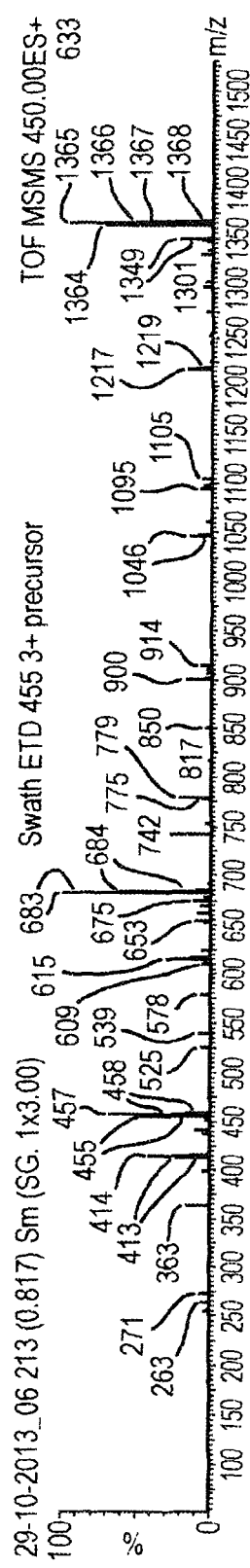
FIG. 2D shows a corresponding ETD fragmentation mass spectrum obtained by subjecting triply charged adduct ions of substance P having a mass to charge ratio of 455 to Electron Transfer Dissociation fragmentation.

FIG. 2D shows Electron Transfer Dissociation fragmentation data obtained by subjecting the Na adduct parent or precursor ion having a mass to charge ratio of 455 to Electron Transfer Dissociation fragmentation.

Embodiment of the present invention solve the problem of obtaining Electron Transfer Dissociation type data in an Data Independent Acquisition mode of operation in which parent or precursor ions having a wide range of mass to charge ratios are fragmented. This would normally be impossible due to the limited charge capacity of an Electron Transfer Dissociation cell. Embodiment of the present invention advantageously provide complementary and specific Electron Transfer Dissociation data during and/or as part of a Data Independent two dimensional MS/MS Collision Induced Dissociation experiment.

Alternative embodiments are contemplated wherein the mass filter may be replaced by and/or combined with or substituted for an ion mobility spectrometer or separator.

In an alternative embodiment, Hi-Lo data (wherein a fragmentation device is repeatedly switched so as to obtain substantially contemporaneous parent or precursor ion mass spectral data and fragment ion mass spectral data) may be used to trigger the second fragmentation mode of operation e.g. the Electron Transfer Dissociation experiment. For example, according to this embodiment when an ion peak of interest or a specific product ion (e.g. a Collision Induced Dissociation fragment ion or product ion) is detected by the Time of Flight mass analyser system or control system, the mass filter may be temporarily programmed to jump to a mass to charge ratio window of interest, whilst the parent or precursor ions preferably undergo fragmentation in the second mode of operation (e.g. Electron Transfer Dissociation fragmentation mode of operation).

According to less preferred embodiments, when ions of interest are detected rather than (or in addition to) switching into a second fragmentation mode of operation, the mass to charge ratio range of ions transmitted into the fragmentation or reaction device may be reduced. It will be appreciated that in this manner, a full, unbiased MS/MS data set over a wide mass to charge ratio range with high-duty cycle can be acquired in the manner discussed above albeit in a sub-optimal manner.

More detailed and accurate fragment data of interest can additionally be obtained in the reduced mass to charge ratio range mode of operation in the same experimental run or acquisition.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
mass filtering parent or precursor ions with a mass filter;
transmitting the mass filtered parent or precursor ions into a fragmentation or reaction device operating in a first fragmentation or reaction mode;
fragmenting or reacting the parent or precursor ions in the fragmentation or reaction device operating in the first fragmentation or reaction mode so as to produce first fragment or product ions;
wherein the mass to charge ratio, or range of mass to charge ratios, of the parent or precursor ions transmitted by the mass filter is varied with time such that parent or precursor ions of different mass to charge ratios are fragmented or reacted by the first fragmentation or reaction mode at different times;
monitoring for the detection of parent or precursor ions of interest and/or first fragment or product ions of interest, and wherein if parent or precursor ions of interest and/or first fragment or product ions of interest are detected then said method further comprises:
halting the variation in the mass to charge ratios transmitted by the mass filter or otherwise operating the mass filter such that the mass to charge ratio, or range of mass to charge ratios, of the parent or precursor ions transmitted by the mass filter is static or remains constant for a first period of time; and then
directing the parent or precursor ions transmitted by the mass filter during said first period of time into a fragmentation or reaction device operating in a second, different fragmentation or reaction mode of operation; and
fragmenting or reacting the parent or precursor ions in the fragmentation or reaction device operating in the second fragmentation or reaction mode so as to produce second fragment or product ions.

2. The method of claim 1, wherein all of the claimed steps are carried out during a single acquisition or experimental run.

3. The method of claim 1, wherein said parent or precursor ions of interest have a mass to charge ratio corresponding to the mass to charge ratio transmitted by the mass filter during said first period of time; and/or wherein the first fragment or product ions of interest are fragment or product ions of the same parent or precursor ions that are transmitted by the mass filter during said first period of time.

4. The method of claim 1, wherein at the end of said first period of time, the method resumes the variation of the mass to charge ratios transmitted by the mass filter and directs the parent or precursor ions transmitted by the mass filter into the fragmentation or reaction device operating in the first fragmentation or reaction mode so as to fragment or react these ions in the first fragmentation or reaction mode to produce first fragment or product ions.

5. The method of claim 4, wherein the variation of the mass to charge ratios transmitted by the mass filter is resumed until a further parent or precursor ion of interest and/or further first fragment or product ion of interest is detected, wherein the method then halts again the variation in the mass to charge ratios transmitted by the mass filter or otherwise operates the mass filter such that the mass to charge ratio, or range of mass to charge ratios, of the parent or precursor ions transmitted by the mass filter is static or remains substantially constant for a second period of time; directs the parent or precursor ions transmitted by the mass filter during the second period of time into the fragmentation or reaction device operating in the second fragmentation or reaction mode; and fragments the parent or precursor ions in the fragmentation or reaction device operating in the second fragmentation or reaction mode so as to produce second fragment or product ions.

6. The method of claim 1, wherein the mass to charge ratio or mass to charge ratio range transmitted by the mass filter is scanned continuously with time, except for said period(s) of time when said ions of interest have been detected; or wherein the mass to charge ratio or mass to charge ratio range of parent or precursor ions transmitted by the mass filter is continually stepped with time, except for said period(s) of time when said ions of interest have been detected.

7. A method of mass spectrometry comprising:
providing parent or precursor ions that are separated according to a physicochemical property;
transmitting the separated parent or precursor ions having different values of the physicochemical property into a fragmentation or reaction device operating in a first fragmentation or reaction mode at different times;
fragmenting or reacting the parent or precursor ions in the fragmentation or reaction device operating in the first fragmentation or reaction mode so as to produce first fragment or product ions;
monitoring for the detection of parent or precursor ions of interest and/or first fragment or product ions of interest, and wherein if parent or precursor ions of interest and/or first fragment or product ions of interest are detected then said method further comprises:
transmitting parent or precursor ions, the parent or precursor ions of interest, or parent or precursor ions of said first fragment or product ions of interest, into a fragmentation or reaction device operating in a second, different fragmentation or reaction mode of operation for a first period of time; and
fragmenting or reacting the parent or precursor ions in the fragmentation or reaction device operating in the second fragmentation or reaction mode so as to produce second fragment or product ions.

8. The method of claim 7, wherein the step of providing parent or precursor ions that are separated according to a physicochemical property is performed by
separating parent or precursor ions in an ion mobility separator; and
wherein the step of transmitting the separated parent or precursor ions having different values of the physicochemical property into the fragmentation or reaction device operating in the first fragmentation or reaction mode at different times is performed by:
transmitting the parent or precursor ions separated by the ion mobility separator into the fragmentation or reaction device operating in the first fragmentation or reaction mode; and
varying the ion mobility, or range of ion mobilities, of the parent or precursor ions transmitted by or from the ion mobility separator with time such that parent or precursor ions of different ion mobilities are fragmented or reacted by the first fragmentation or reaction mode at different times.

9. The method of claim 8, wherein the step of transmitting the parent or precursor ions into the fragmentation or reaction device operating in the second mode of operation comprises maintaining the ion mobility and/or ion mobility range of the parent or precursor ions transmitted by or from the ion mobility separator static or substantially constant for the first period of time.

10. The method of claim 9, wherein at the end of said first period of time, the method resumes the variation of the ion mobilities transmitted by or from the ion mobility separator and directs the transmitted parent or precursor ions into the fragmentation or reaction device operating in the first fragmentation or reaction mode so as to fragment or react these ions in the first fragmentation or reaction mode to produce first fragment or product ions.

11. The method of claim 10, wherein the variation of the ion mobilities transmitted is resumed until a further parent or precursor ion of interest and/or further first fragment or product ion of interest is detected, wherein the method then halts the variation in the ion mobilities transmitted by or from the ion mobility separator or otherwise operates the spectrometer such that the ion mobility, or range of ion mobilities, of the parent or precursor ions transmitted by or from the ion mobility separator is static or remains substantially constant for a second period of time; directs the parent or precursor ions transmitted by or from the ion mobility separator during the second period of time into the fragmentation or reaction device operating in the second fragmentation or reaction mode; and fragments the parent or precursor ions in the fragmentation or reaction device operating in the second fragmentation or reaction mode so as to produce second fragment or product ions.

12. The method of claim 8, wherein said parent or precursor ions of interest have an ion mobility or range of ion mobilities corresponding to the ion mobility or range of ion mobilities transmitted into the fragmentation or reaction device operating in the second fragmentation or reaction mode of operation; and/or wherein the first fragment or product ions of interest are fragment or product ions of the same parent or precursor ions that are transmitted into the fragmentation or reaction device operating in the second fragmentation or reaction mode of operation.

13. The method of claim 7, wherein said step of providing parent or precursor ions that are separated according to a physicochemical property comprises separating an analyte sample in a molecular separator and then ionising the sample eluting from the separator.

14. The method of claim 7, wherein the step of transmitting the ions into the fragmentation or reaction device operating in the second fragmentation or reaction mode of operation corresponds to transmitting only the parent or precursor ions of interest, or transmitting only the parent or precursor ions of said first fragment or product ions of interest, into the fragmentation or reaction device operating in the second mode of operation during the first period of time.

15. The method of claim 7, wherein at the end of said first period of time, the method directs parent or precursor ions having different values of the physicochemical property into the fragmentation or reaction device operating in the first fragmentation or reaction mode so as to fragment or react these ions in the first fragmentation or reaction mode to produce first fragment or product ions.

16. The method of claim 7, wherein:
said first fragmentation or reaction mode of operation comprises a Collisional Induced Dissociation ("CID") mode of operation; and/or
said second fragmentation or reaction mode of operation comprises an Electron Transfer Dissociation ("ETD") mode of operation or an Electron Capture Dissociation ("ECD") mode of operation.

17. The method of claim 7, wherein the rate of charge of the parent or precursor ions entering the fragmentation or reaction device operating in the first fragmentation or reaction mode is a first rate, and the rate of charge of the parent or precursor ions entering the fragmentation or reaction device operating in the second fragmentation or reaction mode is a second, lower rate.

18. The method of claim 7, wherein the step of fragmenting or reacting the parent or precursor ions in the fragmentation or reaction device operating in the second fragmentation or reaction mode is performed immediately after detecting the parent or precursor ions and/or fragment or product ions of interest, or after a period of time but during the same acquisition or experimental run.

19. The method of claim 7, wherein said step of monitoring for the detection of parent or precursor ions of interest comprises monitoring for neutral loss ions of interest.

20. A method of mass spectrometry comprising:
fragmenting or reacting parent or precursor ions having a first mass to charge ratio range in a fragmentation or reaction device operating in a first fragmentation or reaction mode so as to produce first fragment or product ions;
monitoring for parent or precursor ions and/or first fragment or product ions of interest;
wherein if parent or precursor ions and/or first fragment or product ions of interest are detected then said method further comprises:
fragmenting or reacting parent or precursor ions having a second, smaller mass to charge ratio range in a fragmentation or reaction device operating in a second fragmentation or reaction mode so as to produce second fragment or product ions.

* * * * *